US010664701B2

(12) United States Patent
Gerber et al.

(10) Patent No.: US 10,664,701 B2
(45) Date of Patent: May 26, 2020

(54) GAS BUBBLE DETECTOR

(71) Applicant: Medtronic, Inc., Minneapolis, MN (US)

(72) Inventors: Martin T. Gerber, Maple Grove, MN (US); David B. Lura, Maple Grove, MN (US); Shawn Kelley, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 86 days.

(21) Appl. No.: 15/677,536

(22) Filed: Aug. 15, 2017

(65) Prior Publication Data

US 2018/0075299 A1     Mar. 15, 2018

Related U.S. Application Data (60) Provisional application No. 62/385,931, filed on Sep. 9, 2016.

(51) Int. Cl.
| | |
|---|---|
| *G01N 21/53* | (2006.01) |
| *G06K 9/00* | (2006.01) |
| *A61M 1/16* | (2006.01) |
| *G01N 15/02* | (2006.01) |
| *G01N 21/85* | (2006.01) |

(Continued)

(52) U.S. Cl.
CPC ....... *G06K 9/00624* (2013.01); *A61M 1/1658* (2013.01); *G01N 15/0227* (2013.01); *G01N 21/53* (2013.01); *G01N 21/80* (2013.01); *G01N 21/85* (2013.01); *G01N 33/0027* (2013.01); *G06K 9/209* (2013.01); *A61M 1/3626* (2013.01); *G01N 2015/0011* (2013.01)

(58) Field of Classification Search
CPC .............. A61M 1/3626; A61M 1/1658; G06K 9/00624; G06K 9/209; G01N 15/0227; G01N 21/53; G01N 21/80; G01N 21/85; G01N 33/0027; G01N 2015/0011
See application file for complete search history.

(56) References Cited

U.S. PATENT DOCUMENTS

| | | | | |
|---|---|---|---|---|
| 3,754,867 | A | | 8/1973 | Guenther |
| 4,177,573 | A | * | 12/1979 | Boston, III ............ G03B 13/04 33/1 K |

(Continued)

FOREIGN PATENT DOCUMENTS

| | | |
|---|---|---|
| CN | 202048893 | 3/2011 |
| CN | 103439230 A | 9/2013 |

(Continued)

OTHER PUBLICATIONS

European Search Report for App. No. 17190053.3, dated Jan. 2, 2018.

(Continued)

*Primary Examiner* — Eileen M Adams
(74) *Attorney, Agent, or Firm* — Kenneth Collier; Roger Hahn (57) ABSTRACT

The invention relates to a gas bubble detector for determining gas bubbles in a fluid. The gas bubble detector can be used in any application requiring a determination whether gas bubbles exist in the fluid. The gas bubble detector has a photodetector, a light source, and a chamber in which the presence of gas bubbles are detected.

19 Claims, 6 Drawing Sheets

(51) Int. Cl.
*G01N 21/80* (2006.01)
*G01N 33/00* (2006.01)
*G06K 9/20* (2006.01)
*A61M 1/36* (2006.01)
*G01N 15/00* (2006.01)

(56) References Cited

U.S. PATENT DOCUMENTS

| | | | |
|---|---|---|---|
| 4,229,299 A * | 10/1980 | Savitz | A61M 1/1656 210/137 |
| 4,661,246 A | 4/1987 | Ash | |
| 4,772,560 A | 9/1988 | Attar | |
| 5,091,642 A | 2/1992 | Chow | |
| 6,261,233 B1 * | 7/2001 | Kantorovich | A61B 8/06 600/454 |
| 7,207,946 B2 * | 4/2007 | Sirokman | A61M 1/0013 600/529 |
| 2003/0113931 A1 | 6/2003 | Pan et al. | |
| 2005/0214863 A1 | 9/2005 | McDevitt | |
| 2005/0265895 A1 | 12/2005 | Kopelman | |
| 2007/0161113 A1 | 7/2007 | Ash | |
| 2008/0200866 A1 | 8/2008 | Prisco | |
| 2010/0116740 A1 * | 5/2010 | Fulkerson | A61M 1/3652 210/646 |
| 2010/0133189 A1 * | 6/2010 | Maierhofer | A61M 1/1656 210/644 |
| 2011/0081728 A1 | 4/2011 | Putnam | |
| 2012/0135396 A1 | 5/2012 | McDevitt | |
| 2014/0216250 A1 | 8/2014 | Meyer | |
| 2014/0314625 A1 | 10/2014 | Clift | |

FOREIGN PATENT DOCUMENTS

| | | |
|---|---|---|
| WO | WO 1998054563 | 12/1998 |
| WO | WO 20140121161 | 8/2014 |
| WO | WO 20150159280 | 10/2015 |

OTHER PUBLICATIONS

European Search Report for App. No. 17190066, dated Jan. 16, 2018.
European Search Report for App. No. 17190084, dated Feb. 9, 2018.
Wollenstein, et al, "Colorimetric gas sensors for the detection of ammonia, nitrogen dioxide, and carbon monoxide: current status and research trends", Sensor and Test Conference 2011, Jan. 2, 2011, pp. 562-567.
Chinese Office Action for App. No. 2019071601874110, dated Jul. 19, 2019.

* cited by examiner

GAS BUBBLE DETECTOR

CROSS-REFERENCE TO RELATED APPLICATIONS

This application claims the benefit of and priority to U.S. Provisional Patent Application No. 62/385,931 filed Sep. 9, 2016, the entire disclosure of which is incorporated by reference herein.

FIELD OF THE INVENTION

The invention relates to a gas bubble detector for determining the presence of gas bubbles in a fluid. The gas bubble detector can be used in any application requiring a determination as to whether gas bubbles exist in the fluid. The gas bubble detector has a photodetector, a light source, and a chamber in which the presence of gas bubbles are detected.

BACKGROUND

The detection of gas bubbles in a fluid is necessary in several fields and applications. In dialysis, gas bubbles must be removed prior to contacting dialysate with the blood of a patient across a semi-permeable membrane. In fuel lines or hydraulic lines, gas bubbles can damage or decrease efficiency of automobiles or machinery. However, known systems and methods for gas detection require passing a fluid through a fluid tube and determining the presence of bubbles digitally, or physical observation of a fluid line and making a determination as to whether gas bubbles are present. Known systems fail to provide an automated, accurate, and efficient method of determining both the presence of, and size of, gas bubbles in a fluid. Hence, there is a need for a gas bubble detector that can accurately and automatically determine whether gas bubbles exist in a fluid using a gas bubble detection algorithm with minimal human involvement. There is further a need for a gas bubble detector that can accurately determine the presence of gas bubbles of any size, and quantify the size of any gas bubbles detected.

SUMMARY OF THE INVENTION

The first aspect of the invention is drawn to a gas bubble detector. In any embodiment, the gas bubble detector can include at least one fluid inlet and at least one fluid outlet; the fluid inlet and fluid outlet fluidly connectable to a fluid flow path; a mixing chamber fluidly connected to the at least one fluid inlet and at least one fluid outlet; a light source positioned on a first side of the mixing chamber transmitting light through the mixing chamber; a photodetector positioned on a second side of the mixing chamber receiving the transmitted light; and a processor in electronic communication with the photodetector, the processor quantitating a detected bubble size and a bubble contrast from an image captured by the photodetector using a bubble detection algorithm.

In any embodiment, the gas bubble detector can include a first transparent surface positioned between the light source and the mixing chamber and a second transparent surface positioned between the photodetector and the mixing chamber.

In any embodiment, a first light guide can direct light from the light source to the first side of the mixing chamber and a second light guide can direct light received on the second side of the mixing chamber directing light to the camera or photodetector.

In any embodiment, the fluid inlet and fluid outlet can both be positioned on a first side of the mixing chamber.

In any embodiment, a curved flow path can define a fluid flow path from any inlet to any outlet.

In any embodiment, the gas bubble detector can include a magnifying sight between the photodetector and the mixing chamber.

In any embodiment, the first transparent surface can be a clear window or a surface of the light source and the second transparent surface can be a clear window or a portion of the lens of the photodetector.

In any embodiment, the gas bubble detector can include a second fluid outlet fluidly connectable to the fluid flow path.

In any embodiment, the fluid inlet, the first fluid outlet, and the second fluid outlet can each be positioned on a first side of the mixing chamber.

In any embodiment, the processor can quantify a size of one or more gas bubbles.

In any embodiment, the bubble detection algorithm can be an image recognition algorithm.

In any embodiment, the gas bubble detector can include a receiving slot for an aperture card; the receiving slot positioned in the mixing chamber.

In any embodiment, the photodetector can detect ultraviolet light.

In any embodiment, the gas bubble detector can include a receiving slot for a sensor card in fluid communication with the mixing chamber; the sensor card having one or more colorimetric membranes.

In any embodiment, the receiving slot cover lock can include a solenoid rod insertable into a hole in the fluid sensor apparatus.

In any embodiment, the processor can determine a change in a wavelength of light transmitted through the sensor card, an intensity of light transmitted through the sensor card, a wavelength of fluorescent light from the sensor card, or an intensity of fluorescent light from the sensor card.

In any embodiment, the sensor card can have a pH sensing membrane, an ammonia sensing membrane, or combinations thereof.

In any embodiment, the processor can determine a pH and/or ammonia concentration based on the change in the wavelength of light transmitted through the sensor card, the intensity of light transmitted through the sensor card, the wavelength of fluorescent light from the sensor card, or the intensity of fluorescent light from the sensor card.

Any of the features disclosed as being part of the first aspect of the invention can be included in the first aspect of the invention, either alone or in combination.

The second aspect of the invention is drawn to a method. In any embodiment, the method can include flowing fluid through the gas bubble detector of the first aspect of the invention, transmitting light through the fluid in the gas bubble detector; detecting light transmitted through the fluid; and determining the presence of gas bubbles in the fluid with the processor based on the light transmitted through the fluid.

In any embodiment, the method can include quantitating a bubble size of at least one gas bubble in the fluid.

In any embodiment, the step of determining the presence of bubbles in the fluid can include using a bubble detection algorithm.

In any embodiment, the fluid can be dialysate in a dialysate flow path.

In any embodiment, the method can include flowing the dialysate through a degasser prior to flowing the dialysate through the gas bubble detector.

Any of the features disclosed as being part of the second aspect of the invention can be included in the second aspect of the invention, either alone or in combination.

DETAILED DESCRIPTION OF THE INVENTION

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. For example, "an element" means one element or more than one element.

The term "ammonia concentration" refers to the amount of ammonia dissolved in a given amount of a fluid.

An "ammonia sensing membrane" is a substrate with an embedded dye, wherein the dye changes colors in response to ammonia contacting the dye.

The term "aperture card" refers to a component with a hole or window through which light can be transmitted.

The term "bubble contrast" refers to the change in intensity or wavelength of light as a result of the light passing through a gas bubble.

A "bubble detection algorithm" is a digitized method of determining the presence of, or size of, gas bubbles in a fluid based on light received by a photodetector.

The term "bubble size" refers to any measurement of the area or volume of a bubble, and can include a diameter, a radius, or a volume of the bubble.

A "clear window" is a surface through which light can pass with minimal changes to the wavelength(s) and intensity of the light.

A "colorimetric membrane" is any material that can produce a detectable change based on one or more substances in contact with the material. The detectable change can include a visible change such as a change in color, optical transmittance, or a change in emitted fluorescent light intensity or wavelength.

The term "comprising" includes, but is not limited to, whatever follows the word "comprising." Use of the term indicates the listed elements are required or mandatory but that other elements are optional and may be present.

The term "consisting of" includes and is limited to whatever follows the phrase "consisting of" The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "curved flow path" refers to any fluid path defining an arc of any degreed. For example, a curved flow path can refer to fluid flowing in 180° path meaning the fluid flows in a first direction and then flows back in a reverse direction.

A "degasser" is any component or system capable of removing dissolved or undissolved gases from a liquid.

The terms "detecting," "detected," or "to detect" refer to determining a state or characteristic of a system.

The terms "determining" and "determine" refer to ascertaining a particular state of a system or variable(s).

The term "dialysate" describes a fluid into or out of which solutes from a fluid to be dialyzed diffuse through a membrane.

A "dialysate flow path" is the pathway that dialysate will travel when used in normal operation for dialysis.

The terms "electronic communication" or "communication" refer to the ability to transmit electronic information between two components or systems.

The terms "flow," "flowing," and the like refer to a stream of gas, liquid, or combinations thereof moving, issuing, or circulating with a continual change of place among the constituent particles. As used in the phrase "flowing a fluid," the term refers to a stream of liquid.

A "fluid" is a liquid substance optionally having a combination of gas and liquid phases in the fluid. Notably, a liquid, as used herein, can therefore also have a mixture of gas and liquid phases of matter.

The term "fluid flow path" refers to a pathway through which a fluid can travel.

The term "fluid inlet" refers to a conduit or opening through which fluid can enter a component or apparatus.

The term "fluid outlet" refers to a conduit or opening through which fluid can exit a component or apparatus.

The term "fluidly connectable," "fluidly connect," "for fluid connection," "fluid communication," and the like, refer to the ability of providing for passing fluid or gas or mixtures thereof, from one point to another point. The two points can be within or between any one or more of compartments, modules, systems, components, and rechargers, all of any type. The connection can optionally be disconnected and then reconnected.

"Fluorescent light" refers to electromagnetic radiation emitted from a substance stimulated by the absorption of incident radiation.

A "gas bubble" is a pocket of air or gas within a liquid.

The term "gas bubble detector" refers to a system through which a fluid can flow and the presence and/or size of gas bubbles in the fluid determined.

An "image captured by a photodetector" refers to a digital representation of the visible light or fluorescent light detected by the photodetector.

An "image detection algorithm" is an algorithm that determines and identifies a portion of a digital image.

The term "intensity of light" refers to the amplitude of an electromagnetic wave.

The term "lens of the photodetector" refers to a transparent surface on a photodetector for concentrating or dispersing light rays.

A "light guide" refers to a component that can transmit light in a defined path by means of total or near total internal reflectance using reflective surfaces of any type, size, position, and length.

A "light source," "light emitter," "photo emitter," or the like, is any component capable of emitting light at any wavelength including visible, infrared, or ultraviolet light.

A "magnifying sight" is any lens, surface, or other material capable of enlarging an image.

A "mixing chamber" is a space or volume in which one or more liquids, solids, gases, or combinations of liquids, solids, and gases can be mixed.

The terms "quantitating" or to "quantitate" refer to determining a numerical value for a given parameter.

A "photodetector," "camera," and the like is a component capable of detecting light intensity, light composition, or both to result in data, such as an image, of the light detected. The terms "camera" and "photodetector" can also generally refer to any type of detector including an RGB detector or spectrophotometer.

The term "pH" refers to the negative log of the $H^+$ concentration in a fluid when stated in moles of $H^+$ per liter of fluid volume.

A "pH sensing membrane" is a substrate with an embedded dye, wherein the dye changes colors in response to the pH of a fluid.

The term "positioned" or "position" refers to a physical location of a component, feature, or structure.

The term "processor" as used is a broad term and is to be given its ordinary and customary meaning to a person of ordinary skill in the art. The term refers without limitation to a computer system, state machine, processor, or the like designed to perform arithmetic or logic operations using logic circuitry that responds to and processes the basic instructions that drive a computer. In any embodiment of the first, second, third, and fourth invention, the terms can include ROM ("read-only memory") and/or RAM ("random-access memory") associated therewith.

The term "receiving light" or to "receive light" refers to obtaining light at any wavelength or intensity. The received light can be obtained by a sensor, a lens, a camera, a photodetector, or any surface capable of receiving light from a light source.

The term "receiving slot" is a space within a gas bubble detector into which a second component can be placed.

The term "sensor card" refers to a rigid and/or planar component having at least one sensing membrane or sensing material of any kind disposed on, inside or integral to the "sensor card." The sensing membrane or material can contact a fluid, and produce a detectable change in response to a fluid characteristic of the fluid.

A "side of the mixing chamber" refers to a position relative to a mixing chamber.

The term "surface of the light source" refers to the exterior boundary of a light source.

The terms "transmitting light," to "transmit light" or "transmitted light" means to emit light onto or through a substance.

The term "transparent surface" refers to any material through which light can pass but through which fluids cannot pass.

The term "ultraviolet light" refers to electromagnetic radiation having a wavelength generally in a range from about 100 nm to 380 nm.

The term "wavelength of light" refers to the distance between successive crests of an electromagnetic wave.

Gas Bubble Detector

Figure 1A:
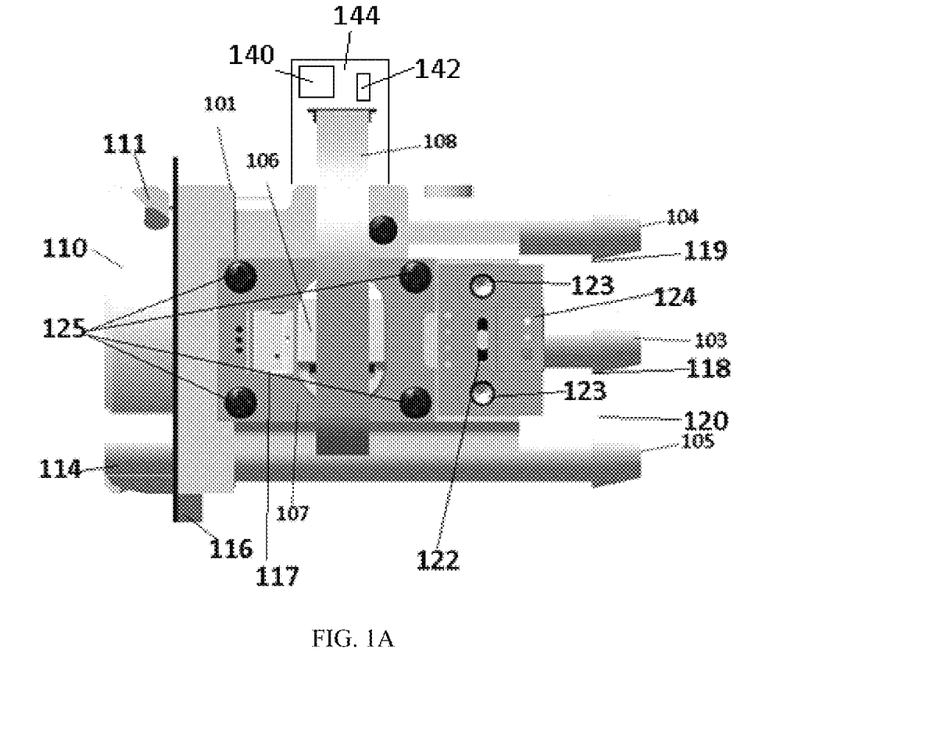
FIGS. 1A-F show a side, perspective, and top view of a gas bubble detector.
Figure 1B:
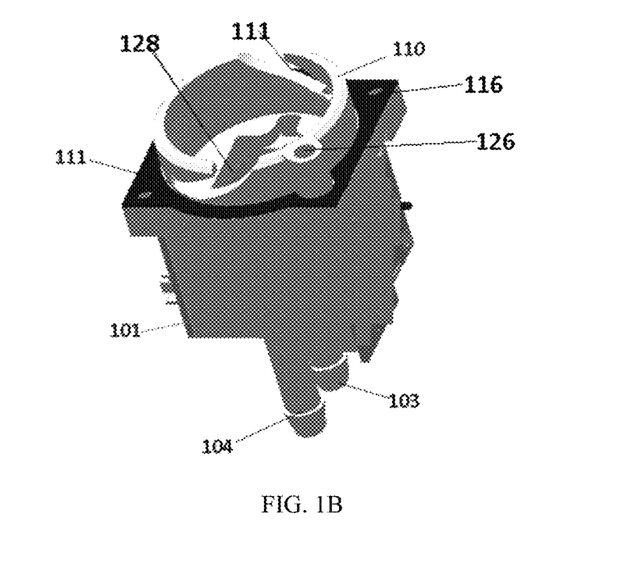
Figure 1C:
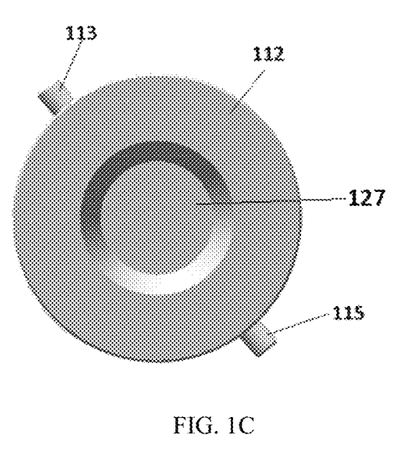
Figure 1D:
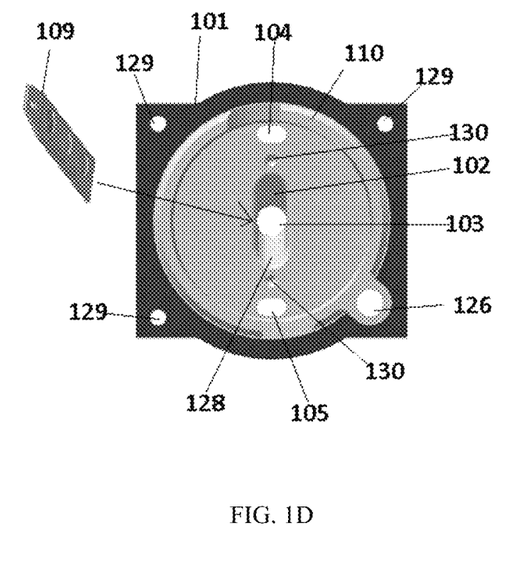
Figure 1E:
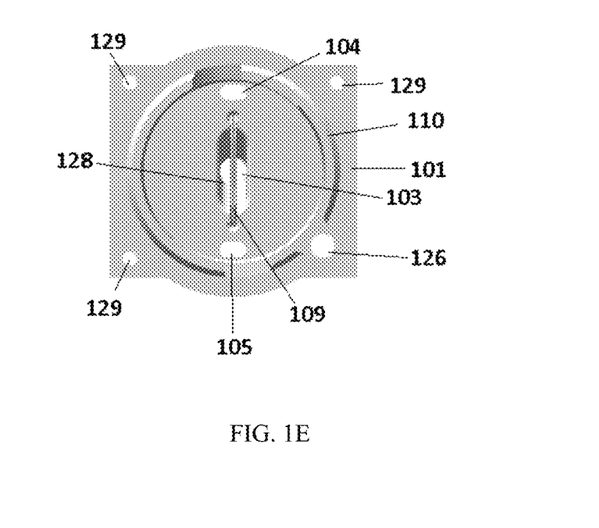
Figure 1F:
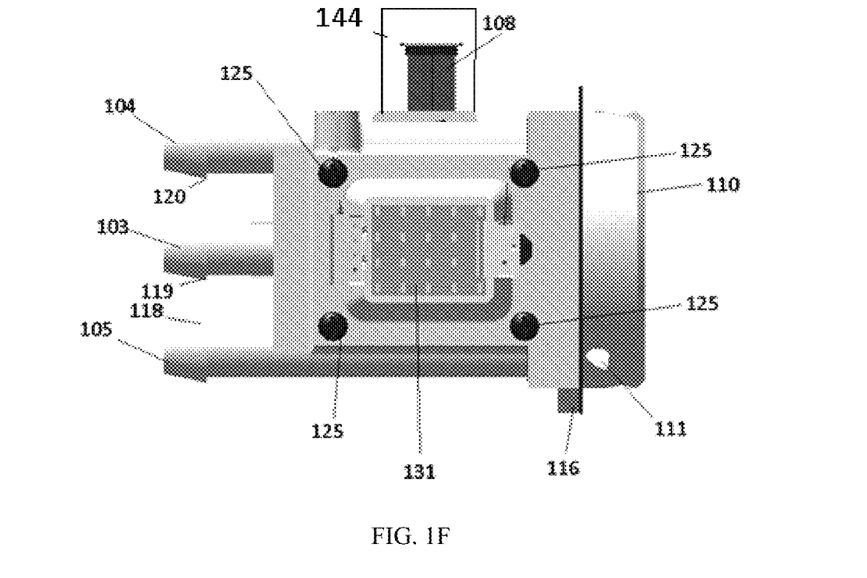

FIGS. 1A-F illustrate a non-limiting embodiment of gas bubble detector 101. FIG. 1A illustrates a side view of the gas bubble detector 101; FIG. 1B illustrates a perspective view of the gas bubble detector 101; FIG. 1C illustrates a receiving slot cover 112 for the gas bubble detector 101; FIG. 1D illustrates a cut-away portion of the gas bubble detector 101 at a specified depth and an aperture card 109 being inserted into a receiving slot 102 of the gas bubble detector 101; FIG. 1E illustrates a front view of the gas bubble detector 101 with the aperture card 109 inserted; and FIG. 1F illustrates a side view of the gas bubble detector 101.

As shown in FIG. 1D, the gas bubble detector 101 can optionally have a receiving slot 102 traversing a mixing chamber 128 along an axis. An optional removable aperture card 109 can be inserted into the receiving slot 102 as illustrated in FIGS. 1D and 1E to a specified depth of the gas bubble detector 101. The removable aperture card can include a window or hole 134 creating an aperture. Indentations 130 on either side of the mixing chamber 128 at the depth of the gas bubble detector 101 in FIG. 1D, can receive an edge of the aperture card 109, to seat or fasten the aperture card 109 in place. At a higher depth of the gas bubble detector 101, a groove can be formed appurtenant to a sidewall of the mixing chamber 128 to receive a side edge of the aperture card 109. An edge of the aperture card 109 can be securely positioned in the mixing chamber 128 at a specified location or orientation with respect to a light source and/or photodetector. Alternatively, one or more grooves can be formed into the gas bubble detector 101 to receive an edge of the aperture card 109 to securely position the aperture card 109 at a specified location or orientation if the aperture card 109 has a width greater than any axis of the mixing chamber 128 as shown in FIG. 1E. Alternatively, the receiving slot and aperture card can be eliminated.

Figure 3:
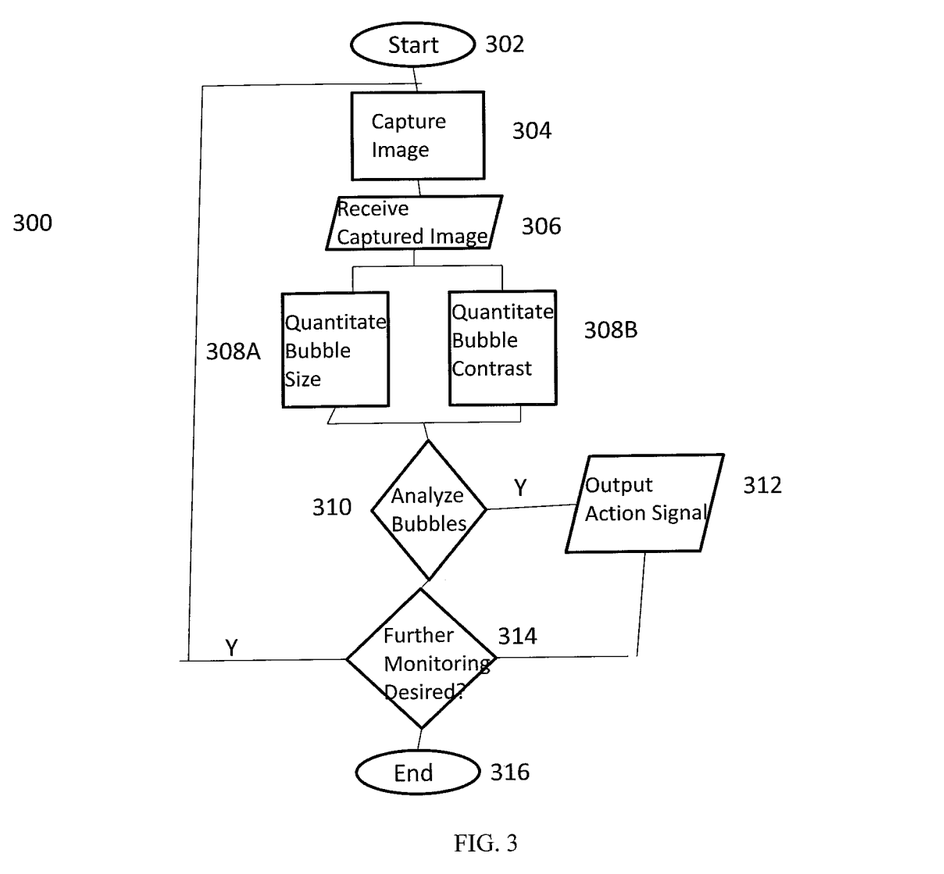
FIG. 3 is a flow chart illustrating a method of detecting gas bubbles in a fluid.

The mixing chamber 128 can optionally have a plurality of transparent windows on the sidewalls as shown in FIG. 3 to provide optical access to the aperture card 109. Holes 129 formed into the body of the gas bubble detector 101 can be used to attach the gas bubble detector 101 to a console or system using screws or other fasteners as shown in FIG. 1D. The mixing chamber 128 extends longitudinally along a length of the receiving slot 102 of the gas bubble detector 101. The receiving slot 102 can extend beyond the mixing chamber 128 and terminate in a fastening mechanism to securely hold the aperture card 109, such as the indentation 130. The mixing chamber 128 can mix fluids to improve bubble detection. Additionally, in a multipurpose bubble detector fluid sensor embodiment, the mixing chamber 128 can mix fluids to improve fluid contact on a sensor card containing colorimetric membranes (not shown). Notably, the mixing chamber 128 defines a volume such that a front side and a back side of the sensor card can be exposed to fluid flow on both sides of the sensor card. The sampled fluid can therefore simultaneously contact a first and second side (or front and back) of the sensor card to advantageously increase the surface area on which fluid contacts sensing membranes in the sensor card. The resulting mixing can result in improved sensing of the fluid by the sensor card. The bubble detector can be a stand alone sensor, optionally with an aperture card, or can be a multi-purpose sensor including a sensor card, and optionally an aperture card. Alternatively, a single aperture/sensor card can be included, the single card having both sensing membranes and an aperture.

In a multipurpose bubble detector fluid sensor embodiment, the sensor card can have at least a pH sensing membrane and an ammonia sensing membrane. Further, the ammonia sensing membrane can be a low sensitivity or high sensitivity membrane. The pH sensing membrane, the ammonia sensing membranes, or both can change color, optical transmittance, or change emitted fluorescent light intensity or wavelength based on a pH or ammonia level of a fluid flowing through the mixing chamber 128. However, the sensor card is not limited to pH and ammonia sensing membranes, and can include any colorimetric membrane producing a detectable change in response to a concentration or other parameter of a fluid. In general, the colorimetric membrane can produce any visible change such as change in color or optical transmittance, or a change in emitted fluorescent light intensity or wavelength, wherein the visible change is detected by the photodetector or camera of the present invention. The sensor card can also include only a pH sensing membrane, only an ammonia sensing membrane, or a sensing membrane having any type of colorimetric membrane.

The sensing membrane has a property reacting to a fluid component that changes an optical parameter depending on the concentration of the component in the fluid. The optical parameter can be any one of color, reflectivity, transitivity fluorescence, adsorption, or any other parameter capable of being optically detected. In a preferred embodiment, the sensing membrane changes color in relationship to changes in the solute concentration of the measured fluid component. For example, the membrane can change color in a first direction along a color spectrum as the solute concentration of the component in the fluid increases, and along a second direction as the solute concentration of the component decreases. The color change of the membrane can be continuous and reversible in response to the component concentration. In the case of an ammonia sensing membrane, a dye can be embedded in a substrate, wherein the dye changes colors in response to an ammonia concentration of a fluid.

Bubbles and optionally color change can be detected by the photodetector through one or more transparent surfaces positioned between a light source and the mixing chamber and the photodetector and mixing chamber. In FIGS. 1A-F, the transparent surfaces are clear windows positioned on the sidewall of the mixing chamber 128. However, the surface of the light source or sources and/or the lens of the photodetector can also or alternatively serve as the transparent surfaces.

In FIG. 1F, one non-limiting example of a light source is shown as LED array 131 connected to the system by electrical connector 117. The LED array 131 can transmit light onto a fluid from a first side of the mixing chamber 128. The light can be directed through the one or more transparent surfaces in the sidewall of the mixing chamber 128. An arrangement of reflective surfaces can be used as a light guide to direct light from an LED array positioned on a side of the gas bubble detector 101 to be transmitted through the mixing chamber 128 and onto the photodetector or camera along any reflectance pathway. For example, a mirror arrangement can guide light to a camera or photodetector such that the camera or photodetector need not be in directly positioned opposite to the light source. The light guide can provide a reflectance pathway such that the camera or photodetector can be positioned in any convenient location to receive the reflected light. Similarly, the LEDs or any light source can rely on a light guide to direct light such that light sources can be conveniently positioned at any position, and need not be opposedly positioned to the camera or photodetector. In one embodiment, both the light source and the camera or photodetector transmit and receive light, respectively, using a light guide. The light source can be any source of light at any wavelength capable of shining light through the mixing chamber 128. In an embodiment, the LED provides white light; however, any color or wavelength of light can be used. In an embodiment, the light source provides uniform backlighting onto one side of the aperture card 109 such that a photodetector 106 (shown in FIG. 1A) positioned on an opposite side of the gas bubble detector 101 can detect bubbles passing between the photodetector and the light source via one or more transparent windows. The LED array 131 can be positioned at any part of the apparatus capable of providing uniform light through the mixing chamber 128, including direct and side-firing or side-emitting LEDs. In general, the transparent windows for the LED array 131 and photodetector 106 can be antipodal to each other. The photodetector 106 can be any appropriate camera, photodetector, spectrophotometer, or photosensor known to those of ordinary skill in the art. In performing image recognition of a bubble in the mixing chamber, consideration of the photodetector's 106 angle of view and focal length can be taken into account relative to the dimensions of the mixing chamber including the optional receiving slot 102 and the light source. The angle of view describes the angular extent of a given scene that can be imaged by a camera. In an embodiment, a high power lens may be provided to detect small bubbles. Alternatively, a magnifying sight, such as a magnifying lens, can be positioned between the photodetector and mixing chamber to enlarge the gas bubbles, enabling detecting of smaller bubbles. In an alternative embodiment, the bubble detection algorithm can be tuned to detect gas bubbles of a particular size. The processor can conduct a pixel scan of the image captured by the photodetector, and the density of the scan can be varied depending on the desired bubble size detection. For example, a more dense pixel scan will detect smaller bubbles.

The photodetector 106 can transmit the image or sensed output to one or more processors in electronic communication with the photodetector 106 for quantitating a detected bubble size and a bubble contrast. In a multipurpose bubble detector fluid sensor embodiment, the one or more processors can further determine the pH or ammonia level of a fluid. The camera or photodetector 106 can also detect fluorescent light emitted from the sensor card. For detection of fluorescent light, an optical bandpass filter can be included in front of the photodetector to allow the emitted fluorescent light to pass to the photodetector while blocking any transmitted light from the LED array. The photodetector can detect any change in the light transmitted including the wavelength of light, the mean intensity of light, the variation in intensity of light, and the pixel location in an image produced by the photodetector.

Although illustrated as opposing the photodetector, the LED array 131 can be positioned anywhere on the gas bubble detector 101, including on any side of the gas bubble detector 101. A light guide can be included to allow light from an LED array positioned on a side of the gas bubble detector 101 to be transmitted through the sensor card and onto the photodetector along any reflectance pathway. For example, a mirror arrangement can guide light to a camera or photodetector such that the camera or photodetector need not be in directly positioned opposite to the light source. The light guide can provide a reflectance pathway such that the camera or photodetector can be positioned in any convenient location to receive the light. Similarly, the LEDs or any light source can rely on a light guide to direct light such that light sources can be conveniently positioned at any position, and need not be opposedly positioned to the camera or photodetector. In one embodiment, both the light source and the camera or photodetector transmit and receive light, respectively, using a light guide.

A grating light valve (not shown) having an adjustable diffraction grating can be included to control the intensity of light diffracted onto the photodetector 106. The diffraction grating can be a set of equally spaced, narrow, parallel grates. The grates can disperse the light at different wavelengths, so that light intensity can be measured as a function of a particular wavelength. The transparent surfaces, such as clear windows, can be free from scratches that degrade the sensor performance. In one non-limiting embodiment, to reduce scratches to the clear windows, the windows can be solvent polished. As shown in FIG. 1F, the photodetector 106 can transmit the image or other sensed output to one or more processors 140 in electronic communication with the photodetector 106 via electronic link 108. As with all features of the present application, intervening components (such as a circuit board 144) can be present between the processor 140 and the photodetector. The processor 140 may be in electronic communication with one or more memories 142. Memory 142 can be any machine-readable storage medium in communication with the processor 140 and can store instructions that when executed by the processor 140 perform the methods herein.

As described, the processor 140 can determine the presence or size of gas bubbles in the mixing chamber 128, as well as the color of the sensing membranes in a multi-purpose sensor, based on the sensed output. Electronics 107 of FIG. 1A can control the photodetector 106 and the light source. Although illustrated as having wired communication links between the photodetector, electronics, and processor, one of skill in the art will understand that any method of transmitting and receiving data can be used, including Bluetooth, Wi-Fi, or any other methods known in the art. The processor can receive data, and in particular the image produced by the photodetector, and determine the intensity of the pixels of a particular color in an image of the sensing membranes. A spectrophotometer, which measures the wavelength and intensity of the transmitted light can also be used. Advantageously, a spectrophotometer can be more specific to a color of light detected. The processor can then determine the presence of and size of any gas bubbles using a bubble detection algorithm. The processor 140 can be housed within, or positioned outside of, the gas bubble detector 101. The photodetector 106 can be operated under manual control or by a software application for controlling the exposure, gain and white balance.

As shown in FIG. 1A, fluid can enter the gas bubble detector 101 through a fluid inlet 103 and into the mixing chamber 128 of FIG. 1D. The fluid can then exit the mixing chamber 128 through fluid outlets 104 and 105. The fluid outlets 104 and 105 and the fluid inlet 103 can be both positioned on the same side of the mixing chamber 128 to provide a curved fluid flow path such that fluid enter through the fluid inlet 103 positioned in between fluid outlets 104 and 105 wherein fluid then flows into a first end of the mixing chamber 128 and flows in a curved flow path and out a second end of the mixing chamber 128 and into the two fluid outlets 104 and 105 positioned on the same side as the mixing chamber 128. Conversely, the two fluid outlets 104 and 105 can be used as inlets to introduce fluid into mixing chamber 128 along a curved flow path such that fluid flows into and out of the fluid inlet 103. One of skill in the art will understand that one or more fluid inlets and outlets can be used. In a preferred embodiment, the two fluid outlets 104 and 105 advantageously improve mixing of the fluid in the mixing chamber 128, which can improve bubble detection accuracy. Notch 118 on fluid inlet 103, notch 119 on outlet 104, and notch 120 on outlet 105 can provide secured fastening of the fluid inlet 103 and fluid outlets 104 and 105 to tubing as needed. In FIG. 1C, the receiving slot 102 can include additional components to ensure that the detachable mixing chamber cover 112 fits tightly over the receiving slot 102 and does not move as fluid is flowed into and through the mixing chamber 128. As illustrated in FIGS. 1A and 1B, the receiving slot 102 can have an extended portion 110 that will contact the mixing chamber cover 112 when closed. The extended portion 110 can include grooves 111 and 114 for receiving pins 113 and 115 when the mixing chamber cover 112 is placed over the mixing chamber 128. The pins 113 and 115 engage with the grooves 111 to ensure the mixing chamber cover 112 is properly placed and securely fastened on the gas bubble detector 101.

When used with an aperture card and/or sensor card, the card 109 can be fixed into a specified position and/or orientation inside the receiving slot 102 to resist any movement due to the flow of the fluid. Any suitable fastener to fix the mixing chamber cover 112 to the gas bubble detector 101 is contemplated. Magnets can be placed within the mixing chamber cover 112 and the gas bubble detector 101. If the mixing chamber cover 112 is closed, the magnets can provide a means to determine if cover 112 is closed over the receiving slot 102 on the gas bubble detector 101. As shown in FIG. 1F, overhang 116 can provide support for the receiving slot cover 112 when closed. In FIGS. 1D and 1E, opening 126 on extended portion 110 can provide for a fastener to be inserted through the receiving slot cover 112 to secure the receiving slot cover 112 onto the gas bubble detector 101. In FIG. 1C, an annular bevel 127 can be formed on the mixing chamber cover 112 to capture the aperture card 109 and hold the aperture card 109 securely locked in the gas bubble detector 101. Screws 125 fasten the electronics and photodetector 106 to the gas bubble detector 101. Alternative methods of securing components to the gas bubble detector 101 can be used, including adhesive, glue, bolts, or any other securing components known in the art. Holes 123 allow additional components and electronics to be added to the gas bubble detector 101.

Figure 2:
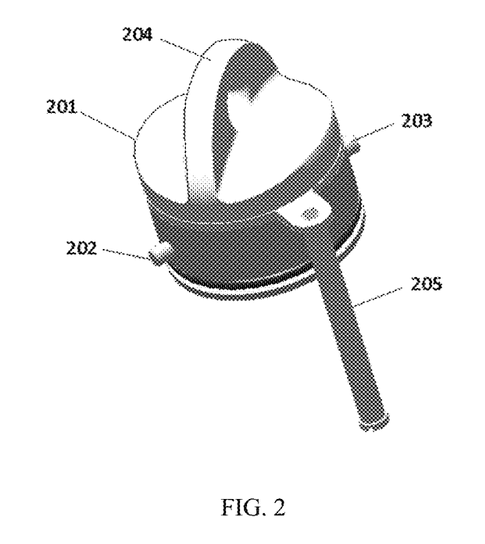
FIG. 2 shows a mixing chamber top for a gas bubble detector.

FIG. 2 illustrates a close-up view of a mixing chamber cover 201 of the gas bubble detector 101. As described, the mixing chamber cover 201 can include pins 202 and 203 to hold the mixing chamber cover 201 in place on the gas bubble detector 101 (FIG. 1A). The mixing chamber cover 201 can also include a handle 204 to facilitate twisting of the mixing chamber cover 201 for attachment and detachment of the mixing chamber cover 201 to the gas bubble detector 101. A sliding rod 205 can be included as a means to secure the mixing chamber cover 201 when the mixing chamber cover is open on the gas bubble detector 101 and to prevent the cover from being removed during use. When used with an aperture card, the aperture card can be fixed regarding the mixing chamber cover 201 to ensure that the aperture card does not move within the receiving slot 102 of FIG. 1D as fluid flows over the aperture card. Fixing the aperture card within the gas bubble detector 101 provides the photodetector 106 (FIG. 1A) with a constant focal length, increasing the accuracy of the sensor. Additionally, a bevel 127 (FIG. 1C) can be included on an interior surface of the mixing chamber cover 201 for fixing the aperture card in place. The sensor card can be inserted into the bevel to lock the aperture card in a fixed position and to prevent insertion of the aperture card at a 180° rotation from the intended configuration. The bevel can only allow the aperture card to be inserted into the gas bubble detector in a single configuration. The bevel can be sized and shaped to conform to an edge of the aperture card, fixing the aperture card in position when placed into the bevel. The distance from the aperture card to the photodetector 106 can be any length, including between 15 and 20 mm. The lens of the photodetector can be configured with a focal length equal to the fixed distance between the photodetector 106 and aperture card.

The presence and/or size of gas bubbles in a fluid can be determined by the processor using a bubble detection algorithm[A2]. The bubble detection algorithm can be any algorithm capable of determining the difference between gas bubbles and the surrounding fluid. One example of a bubble detection algorithm is image detection algorithm. Image detection algorithms analyze a digital image to determine patterns in the image. The change in contrast of light that passes through a gas bubble as compared to light only passing through a fluid can be quantitated by the image detection algorithm. The presence of bubbles can be detected based on areas within the image of different contrasts. Based on the magnitude of the change, or the area of the image with a different contrast, the processor can also determine the size of the bubbles.

The operation of a gas bubble detector, such as the gas bubble detector 101 of FIGS. 1A-F is now described with reference to FIG. 3, which discloses a method 300 for detecting gas bubbles in a fluid. In operation 302, the method 300 may be initiated. The gas bubble detector can be fluidly connected to a fluid flow path and fluid may be introduced into the mixing chamber 128, or may already be flowing through the mixing chamber 128. Fluid enters through the fluid inlet 103, into the mixing chamber 128 and out through the fluid outlets 104, 105. In operation 304, an image of the fluid in the mixing chamber may be captured. The light source 131 can be positioned on one side of the mixing chamber. The light source 131 may transmit light through the mixing chamber 128. The photodetector 106 can be positioned on a second side of the mixing chamber 128. The photodetector 106 can receive the transmitted light. The captured image may be digitally stored.

Figure 4:
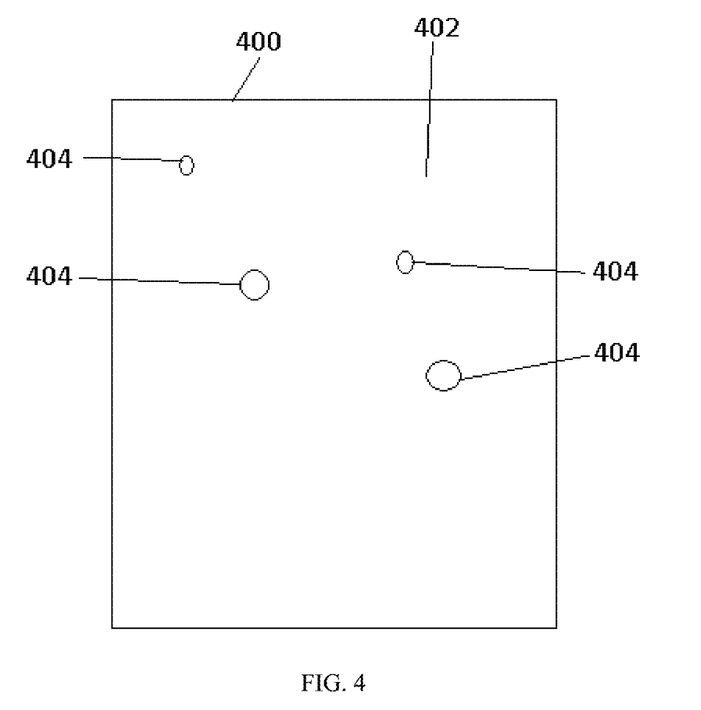
FIG. 4 is a representative drawing of an image captured by a photodetector containing bubbles in a fluid.

In operation 306, the captured image may be transmitted to the one or more processors 140 through the electronic link 108 and the circuit board 140. The one or more processors 306 may execute instructions from memory 142 to execute an image recognition application to recognize the presence of one or more bubbles in the fluid in the mixing chamber. In general, the presence of gas bubbles in a fluid will affect absorption or refraction of light from the light source 131 as captured by the photodetector 106. The different absorption or refraction of light created by a bubble will result in an area in the captured image having a different contrast relative to the fluid. In one non-limiting embodiment, the image recognition application may recognize the presence of a bubble in the captured image based on the contrast of the bubble relative to the fluid as shown in FIG. 4. One of ordinary skill in the art will recognize that specific wavelengths such as ultraviolet light wavelengths may be effective in increasing the contrast between bubbles and the surrounding liquid. However, any wavelength of light that will generate a different contrast between the bubbles and surrounding liquid can be used.

In operation 308A, the image recognition application may quantitate a detected bubble size from the captured image. The image recognition application can quantitate a detected bubble size taking into account the photodetector's angle of view and focal length in measuring the size of the bubble. The size of the photodetector's field of view can be known, allowing quantitation of the bubble size based on the area of the image having a contrast indicating the presence of a gas bubble. In operation 308B, the image recognition application may quantitate a bubble contrast to detect the presence of a gas bubble from an image captured by the photodetector 106. Optionally, the image recognition software may enhance the contrast of the bubble to assist in identifying the bubble in situations where the contrast between the bubble and the fluid is low.

In operation 310, any bubbles detected by the gas bubble detector may be further analyzed to determine the size, number, and/or volume of gas bubbles in the fluid. A determination may be made whether the bubble size and/or contrast matches a predetermined criterion for action being taken. For example, if the bubble(s) are over a certain size, an action may be desirable to provide a warning though an output interface, or to stop a current process involving the fluid. When used in a dialysate flow path, the presence of gas bubbles detected downstream of a degasser may indicate a non-functioning degasser and an ongoing dialysis session can be stopped. When used in fuel lines, the presence of bubbles may indicate leaks, necessitating shutdown of the system. The gas bubble detector can be used in any application where gas bubbles may be detected, with the result of detection of gas bubbles varying with the application. If during operation 310, a determination is made that the bubble size and/or contrast matches a predetermined condition, then the method 300 may proceed to operation 312.

In operation 312, an action signal may be output from the one or more processors 140 to an appropriate system component. For example, if the gas bubble detector 101 is part of a dialysis system having a display, a signal displaying a warning regarding the presence of bubbles may be sent to the display. Additionally and/or alternatively, a signal ending a current dialysis session may be sent to the dialysis system. If during operation 310, a determination is made that the bubble size and/or contrast does not match a predetermined condition, or if no bubbles are detected, then the method 300 may proceed to operation 314.

In operation 314, a determination may be made whether further monitoring using the gas bubble detector 101 is desired. If during operation 314, a determination is made that further monitoring is desired, then the method 300 may return to operation 304 and a new image may be captured. Alternatively, the photodetector can continuously capture images, and no separate determination need be made. If during operation 314, a determination is made that further monitoring is not desired, then the method may return to operation 316 and end.

FIG. 4 is a schematic representation of a captured image 400 of a fluid 402 passing between the photodetector 106 and an aperture card in the mixing chamber 128. The captured image 400 shows bubbles 404 in the fluid 402. Light passing through the bubbles 404 will have a different contrast than light passing only through the surrounding fluid 402. Based on the different contrast, the image recognition algorithm can determine the presence of, and optionally the size of, bubbles 404.

The gas bubble detector can be used in any application where the presence of bubbles needs to be known, eliminated or mitigated. For example, in a dialysis flow path, the gas bubble detector can detect a non-operable or malfunctioning degasser. Dialysate can be flowed through a degasser, and then flowed through the gas bubble detector. Bubbles in the dialysate after passing through the degasser would indicate that the degasser is not properly removing gas from the dialysate. The gas bubble detector can also detect air in the blood of a patient. Further, the gas bubble detector can determine whether priming of the system is complete, as no air should remain in the fluid lines after priming. However, the gas bubble detector can be used in any application by fluidly connecting the gas bubble detector to any fluid flow path, including detection of gas bubbles in fuel lines, hydraulic lines, or anywhere there is active removal of gas from a liquid. The gas bubble detector can work with any fluid transparent enough for light to effectively pass through the fluid. The gas bubble detector can be used as a control mechanism to limit the amount of gas in a fluid, a failure mode detection to detect a non-operable degasser, or a quality control mechanism to ensure that gas is properly being removed from the fluid.

One skilled in the art will understand that various combinations and/or modifications and variations can be made in the described systems and methods depending upon the specific needs for operation. Features illustrated or described as being part of an aspect of the invention may be used in the aspect of the invention, either alone or in combination.

We claim:

1. A gas bubble detector, comprising:
   at least one fluid inlet and at least one fluid outlet; the fluid inlet and fluid outlet fluidly connectable to a fluid flow path;
   a sampling chamber fluidly connected to the at least one fluid inlet and at least one fluid outlet;
   a light source positioned on a first side of the sampling chamber transmitting light into the sampling chamber;
   a photodetector positioned on a second side of the sampling chamber receiving transmitted light or reflected light;
   a processor in electronic communication with the photodetector, the processor quantitating a detected bubble size, a bubble quantity, and/or a bubble contrast from an image captured by the photodetector using a bubble detection algorithm;
   a receiving slot for an aperture card; the receiving slot positioned in the sampling chamber; the aperture card having a hole or a window through which light can be transmitted, and
   a second fluid outlet fluidly connectable to the fluid flow path.

2. The gas bubble detector of claim 1, further comprising a first transparent surface positioned between the light source and the sampling chamber and a second transparent surface positioned between the photodetector and the sampling chamber.

3. The gas bubble detector of claim 2, wherein the first transparent surface is a clear window or a surface of the light source and the second transparent surface is a clear window or a portion of the lens of the photodetector.

4. The gas bubble detector of claim 3, the processor quantifying a bubble size, a bubble quantity, and/or a bubble volume, of one or more gas bubbles.

5. The gas bubble detector of claim 3, wherein the bubble detection algorithm is an image recognition algorithm.

6. The gas bubble detector of claim 1, wherein the fluid inlet and fluid outlets are positioned on a first side of the sampling chamber.

7. The gas bubble detector of claim 1, further comprising a curved flow path defining a flow path from any inlet to any outlet.

8. The gas bubble detector of claim 1, wherein the light source is positioned on the first side of the sampling chamber opposite to the camera or photodetector positioned on the second side of the sampling chamber.

9. The gas bubble detector of claim 1, further comprising a first light guide directing light from the light source to the first side of the sampling chamber and a second light guide directing light received on the second side of the sampling chamber directing light to the photodetector.

10. The gas bubble detector of claim 1, further comprising a magnifying sight between the photodetector and the sampling chamber.

11. The gas bubble detector of claim 1, wherein the fluid inlet, the first fluid outlet, and the second fluid outlet are positioned on a first side of the sampling chamber.

12. The gas bubble detector of claim 1, wherein the photodetector detects ultraviolet light or visible light.

13. The gas bubble detector of claim 1, further comprising a receiving slot for a sensor card in fluid communication with the sampling chamber; the sensor card having one or more colorimetric membranes.

14. The gas bubble detector of claim 13, the processor determining a change in a wavelength of light transmitted through the sensor card, an intensity of light transmitted through the sensor card, a wavelength of fluorescent light from the sensor card, or an intensity of fluorescent light from the sensor card.

15. The gas bubble detector of claim 14, wherein the sensor card comprises a pH sensing membrane, an ammonia sensing membrane, or combinations thereof.

16. The gas bubble detector of claim 15, the processor determining a pH and/or ammonia concentration based on the change in the wavelength of light transmitted through the sensor card, the intensity of light transmitted through the sensor card, the wavelength of fluorescent light from the sensor card, or the intensity of fluorescent light from the sensor card.

17. The gas bubble detector of claim 1, wherein the processor detects bubbles with a diameter of between 0.5 to 3.0 mm, between 0.5 and 1.0 mm, between 0.75 and 1.0 mm, between 1.0 and 1.5 mm, between 1.0 and 2.0 mm, between 1.5 and 2.5 mm, or between 2.0 and 3.0 mm.

18. A method of detecting gas bubbles in a fluid, comprising:
    flowing fluid through the gas bubble detector of claim 1;
    transmitting light through the fluid in the gas bubble detector;
    detecting light transmitted through the fluid; and
    determining the presence of gas bubbles in the fluid with the processor based on the light transmitted through the fluid.

19. The gas bubble detector of claim 1, the processor outputting a signal, wherein the signal is a signal selected from a group consisting of a warning regarding a presence of bubbles, a signal ending a dialysis session, a determination that the detected bubble size or the bubble contrast does not match a predetermined condition, and a determination that no bubbles are detected.

* * * * *